United States Patent [19]

Belliotti et al.

[11] Patent Number: 5,143,929

[45] Date of Patent: Sep. 1, 1992

[54] 2-SUBSTITUTED THIAZOLIDINONE, OXAZOLIDINONE, AND IMIDAZOLIDINONE DERIVATIVES OF FENAMATES AS ANTIINFLAMMATORY AGENTS

[75] Inventors: Thomas R. Belliotti, Ypsilanti; Diane H. Boschelli, Plymouth; David T. Connor, Ann Arbor; Catherine R. Kostlan, Saline, all of Mich.

[73] Assignee: Warner-Lambert Company, Morris Plains, N.J.

[21] Appl. No.: 697,822

[22] Filed: May 9, 1991

[51] Int. Cl.$^5$ ................. C07D 277/34; C07D 277/36; C07D 277/54; A61K 31/425
[52] U.S. Cl. .................... 514/364; 548/183; 548/184; 548/225; 548/226; 548/311
[58] Field of Search ................. 548/183, 184; 514/369

[56] References Cited

U.S. PATENT DOCUMENTS

| | | | |
|---|---|---|---|
| 3,719,480 | 3/1973 | Brantly et al. | 548/184 |
| 4,173,577 | 11/1979 | Sallmann et al. | 548/184 |
| 4,464,382 | 8/1984 | Tanouchi et al. | 548/184 |
| 4,981,865 | 1/1991 | Belliotti et al. | 548/184 |

FOREIGN PATENT DOCUMENTS

| | | |
|---|---|---|
| 0211670 | 2/1987 | European Pat. Off. . |
| 0371438 | 6/1990 | European Pat. Off. . |
| 3023349 | 1/1982 | Fed. Rep. of Germany . |
| 60167999 | 2/1987 | Japan . |

OTHER PUBLICATIONS

Derwent Abstract 86–059691/09–Japanese Patent Application J61012-674-A.
Derwent Abstract 87-307841/44–Denmark Patent Application DE 3713-094-A.
International Journal of Sulfur Chemistry, A, vol. 2, No. 1, 1972; pp. 261-266, T. R. Bosin et al.
Chemical Abstracts, vol. 75, No. 1, May 7, 1971, Abstract No. 5769r and Farmatsevtichnij Zhurual, vol. 25, No. 6, 1970, pp. 3-5, N. E. Plevachuk (and translation attached).
Yakugaku Zasshi, vol. 92, 1972, pp. 490-497, M. Gosha et al. (and translation attached).
J. Pharm. Soc. Jap., vol. 76, 1956, pp. 154-157, H. Taniyama (with translation attached).
Egyptian Journal of Chemistry, vol. 26, 1983, pp. 301-311, H. H. Moharram et al.
Chemical & Pharmaceutical Bulletin, vol. 34, 1986, pp. 1619-1627, J. Katsumi et al.
Chemical Reviews, vol. 61, pp. 463-521, F. C. Brown, Feb. 1961.
Patent Abstract of Japan, unexamined application, Section C, vol. 10, No. 156, Jun. 5, 1986, p. 126C674, Kokaino 61-12 674, Jan. 21, 1986.

*Primary Examiner*—Robert Gerstl
*Attorney, Agent, or Firm*—Joan Thierstein

[57] ABSTRACT

The present invention is for selected novel compounds which are 2-substituted thiazolidinone, oxazolidinone, and imidazolidinone derivatives of fenamates, as well as pharmaceutical compositions and methods of use thereof. These compounds exhibit activity useful in treating allergies and inflammation.

20 Claims, No Drawings

2-SUBSTITUTED THIAZOLIDINONE, OXAZOLIDINONE, AND IMIDAZOLIDINONE DERIVATIVES OF FENAMATES AS ANTIINFLAMMATORY AGENTS

BACKGROUND OF THE INVENTION

The present invention is novel compounds which are 2-substituted thiazolidinone, oxazolidinone, and imidazolidinone derivatives of fenamic acids and pharmaceutically acceptable acid addition or base salts thereof, pharmaceutical compositions and methods of use thereof. The invention compounds are now found to have activity as inhibitors of one or both of 5-lipoxygenase and cyclooxygenase providing treatment of conditions advantageously affected by such inhibition including inflammation, arthritis, pain, fever and the like. Thus, the present invention is also a pharmaceutical composition or method of use thereof.

Although fenamates are known antiinflammatory agents and various 2-substituted thiazolidinones, oxazolidinones, or imidazolidinones are known as useful substituents in other antiinflammatory agents. For example, together with 3,5 di-tertiary-butyl-4-hydroxyphenyl groups as disclosed in EP application No. 89 109406.2 and U.S. patent application 499,937 (incorporated herein by reference), the present combination of ring systems, substituents and moieties is not among those previously known.

The following references disclose compounds which contain a single phenyl group, substituted or unsubstituted, attached to a heterocyclic ring structure, through a methylene bridge:

Japanese patent application J6 1012-674-A (Derwent Abstract 86-059691/09) discloses an imidazolidinone compound of the structure

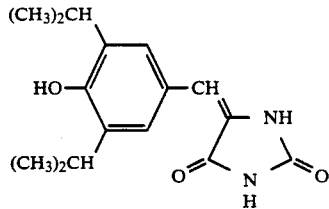

with utility as an antiallergic. It lacks the fenamate structure present in the compounds claimed herein.

Denmark patent application DE 3713-094-A (Derwent Abstract 87-307841/44) discloses benzylidene compounds of which compounds of the structure

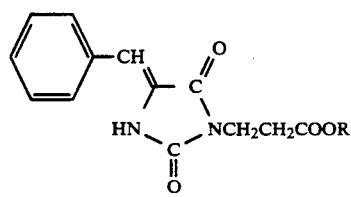

are included, wherein R is 1–18 C straight chain alkyl or 3–18 C branched or cyclic alkyl. These compounds lack the fenamate structure present in the compounds claimed herein. U.S. Pat. No. 4,464,382 discloses compounds of the formula

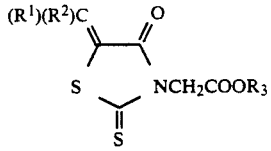

wherein (I) $R^1$ and $R^2$ are taken together to represent a tetramethylene or pentamethylene group, (II) $R^1$ represents a hydrogen atom, and $R^2$ represents (1) a cycloalkyl or cycloalkenyl group of 4–7 carbon atoms which is unsubstituted or substituted by at least one alkyl group of 1–4 carbon atoms, (2) an anthryl or naphthyl group, (3) a phenyl group which is unsubstituted or substituted, p. 2 (4) a heterocyclic group containing at least one of nitrogen, oxygen, and sulfur atoms which is unsubstituted or substituted (5) a

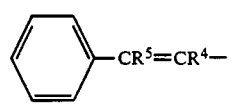

group (wherein $R^4$ represents a hydrogen atom, a halogen atom, phenyl group, or an alkyl group of 1–5 carbon atoms; and $R^5$ represents a hydrogen atom, a phenyl group, or an alkyl group of 1–5 carbon atoms) or

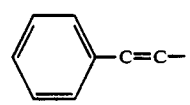

group; or (III) $R^1$ and $R^2$, which may be the same or different with each other, each represents a phenyl group which is unsubstituted or substituted; and $R^3$ represents a hydrogen atom, an alkyl group of 1–12 carbon atoms, an aralkyl group of 7–13 carbon atoms, a cycloalkyl or cycloalkenyl group of 4–7 carbon atoms which is unsubstituted or substituted by at least one alkyl group of 1–4 carbon atoms, or a phenyl group which is unsubstituted or substituted, possess a strong inhibitory activity on aldose reductase.

Bosin and Campaigne, *Intnt'l. J. of Sulfur Chem.*, Vol. 2, p. 262 (1972) disclose compounds of the formula

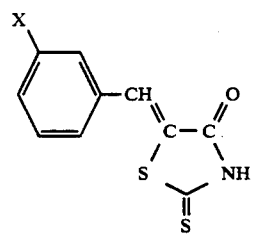

wherein X is F or Cl. These compounds also lack the fenamate structure of the present invention.

Four references, U.S. Pat. Nos. 4,173,577; 4,029,815; 4,981,865; and Japanese application publication 24578/67; all disclose fenamate compounds. None of these references, however, discloses oxazolidinone, imidazolidinone, or thiazolidinone derivatives claimed herein.

U.S. Pat. No. 3,719,480 discloses 4-benzylidenerhodanines which differ from the present invention by a paraphenylamino substitution compared to an ortho such substituent. The utility of this patent is as an electrophotographic composition.

Within these disclosures are uses for treating inflammation as are found here, but the differences between known compounds and the present compounds are readily apparent, with no teaching to make obvious that such differences would also be useful for treatment of the conditions taught here.

SUMMARY OF THE INVENTION

The present invention is a compound of the formula (I)

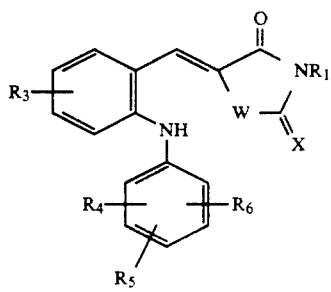

I or a pharmaceutically acceptable salt thereof; wherein
(1) X is oxygen, sulfur, or NH;
(2) W is oxygen, sulfur, or $NR_2$, wherein $R_2$ is hydrogen or lower alkyl;
(3) $R_1$ is lower alkyl or $CH_2COOR_2$, wherein $R_2$ is as defined above;
(4) $R_3$, $R_4$, $R_5$, and $R_6$ are independently
  i) hydrogen;
  ii) fluorine;
  iii) chlorine;
  iv) bromine;
  v) iodine;
  vi) trifluoromethyl;
  vii) lower alkyl;
  viii) CN;
  ix) hydroxy;
  x) lower alkoxy;
  xi) $NO_2$;
  xii) $NR_7R_8$ wherein $R_7$ and $R_8$ are independently hydrogen, lower alkyl or acyl;
  xiii) $S(O)_n$-lower alkyl wherein n is an integer of 0-2.

The present invention is also a compound of the formula (II)

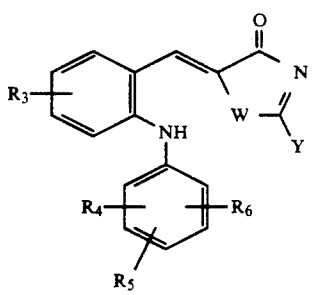

II or a pharmaceutically acceptable salt thereof; wherein
(1) Y is
  i) OH;
  ii) SH;
  iii) $NH_2$;
  iv) $SR_9$ wherein $R_9$ is lower alkyl or $CH_2COOR_{10}$, wherein $R_{10}$ is hydrogen or lower alkyl;
  v) $S(O)n\ R_9$ wherein n and $R_{10}$ are as defined above;
  vi) $NR_9R_{10}$ wherein $R_9$ and $R_{10}$ are as defined above;
  vii) NHCN;
  viii) $NHC(X)NHR_{10}$ wherein X and $R_{10}$ are as defined above;
  ix) $NR_{10}(OR_{11})$ wherein $R_{10}$ is as defined above and $R_{11}$ is hydrogen or lower alkyl;
  x) $NHNHC(S)NH_2$;
  xi) $NHNHC(NH)NH_2$;
(2) W is as defined above
(3) $R_3$, $R_4$, $R_5$, and $R_6$ are as defined above.

The present invention is also a pharmaceutical composition for the treatment of conditions advantageously affected by the inhibition of one or both of 5-lipoxygenase and cyclooxygenase which comprises an amount effective for the treatment of the condition of a compound of formula I or formula II or the pharmaceutically acceptable acid addition or base salt thereof together with a pharmaceutically acceptable carrier. Thus, the compounds of this invention are inhibitors of the synthesis of the products of one or both of the enzymes 5-lipoxygenase and cyclooxygenase, and are for the treatment of the conditions meant to include rheumatoid arthritis, osteoarthritis, other inflammatory conditions, psoriasis, pain, allergic diseases, asthma, inflammatory bowel disease, GI ulcers, cardiovascular conditions including ischemia-induced cell damage, particularly brain damage caused by stroke. These conditions can also include acne, sunburn, psoriasis, and eczema. Such conditions are exemplary in nature and are in no way meant to limit the scope of the invention.

The present invention is also a method for treatment of the condition as noted above in a mammal, including humans, suffering therefrom with a compound of formula I or II or the pharmaceutically acceptable acid addition or base salt thereof, in unit dosage form. The invention also provides for use of any such compound of formula I or II or salt thereof in the manufacture of a medical therapeutic agent.

Pharmaceutical composition or use of the compound or salt of formula I or II is meant to include treatment understood to be prophylactic pertinent to the foregoing named conditions.

The preferred compounds of the present invention are of the formula II wherein $R_3$ is H; $R_4$, $R_5$, and $R_6$ are 2,6-dichloro, 3-methyl or 3,5-di-t-butyl-4-OH; W is sulfur; and Y is NHCN or SH.

The most preferred compound is of the formula II wherein $R_3$ is H; $R_4$, $R_5$, and $R_6$ is 2,6-dichloro-3methyl and Y is NHCN.

DETAILED DESCRIPTION OF THE INVENTION

In compounds of formula I or II, the term "lower alkyl" includes an alkyl group of from one to six carbons such as methyl, ethyl, propyl, butyl and the like and isomers thereof. "Lower alkoxy" means an alkoxy group of from one to six carbons such as methoxy, ethoxy, propoxy, butoxy and the like and isomers thereof. Acyl is from two to four carbon atoms such as acetyl, propionyl, butyryl, and isomers thereof, and benzoyl. "Halogen" is chloro, bromo, fluoro, or iodo.

The compounds of formula II where Y is OH, SH, $NH_2$, NHCN, $NHR_{10}$ or $NHR_{11}$ can exist as tautomers. These tautomers are represented as II' and II":

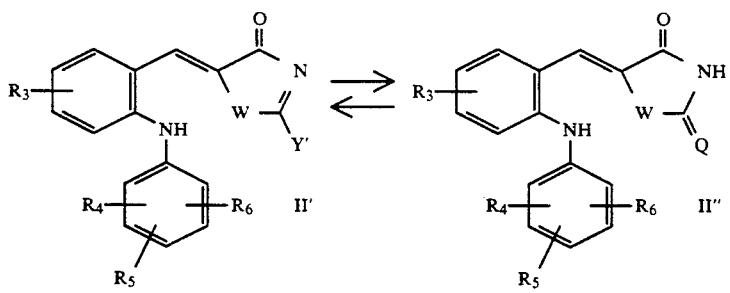

wherein Y', is OH, SH, $NH_2$, NHCN, $NHR_{10}$, or $NHR_{11}$ and Q is oxygen, sulfur, NH, NCN, $NR_{10}$ or $NR_{11}$, respectively, and $R_3$, $R_4$, $R_5$, $R_6$, and W are as defined above.

Appropriate compounds of formula I or II are useful in free base form, in the form of base salts where possible, and in the form of acid addition salts. The three forms are within the scope of the invention. In practice, use of the salt form amounts to use of the base form. Pharmaceutically acceptable salts within the scope of the invention may be those derived from mineral acids such as hydrochloric acid and sulfonic acid; and organic acids such as ethanesulfonic acid, benzenesulfonic acid, p-toluenesulfonic acid, and the like, giving the hydrochloride, sulfonate, ethanesulfonate, benzene sulfonate, p-toluenesulfonate, and the like, respectively; or those derived from bases such as suitable organic and inorganic bases. Examples of pharmaceutically acceptable base addition salts with compounds of the present invention include organic bases which are nontoxic and strong enough to form such salts. These organic bases form a class whose limits are readily understood by those skilled in the art. Merely for purposes of illustration, the class may be said to include mono-, di-, and trialkylamines such as methylamine, dimethylamine, and triethylamine; mono-, di-, or trihydroxyalkylamines such as mono-, di-, or triethanolamine; amino acids such as arginine and lysine; choline; guanidine; Nmethylglucosamine; N-methylglucamine; L-glutamine; N methylpiperazine; morpholine; ethylene diamine; N benzylphenethylamine; tris (hydroxymethyl) amino ethane; and the like. (See for example, "Pharmaceutical Salts," *J. Pharm. Sci.*, 66 (1):1-19 (1977).). Salts of inorganic bases include sodium, potassium, calcium or the like.

The acid addition salts of said basic compounds are prepared either by dissolving the free base or acid of compound I or II in an aqueous or aqueous alcohol solution or other suitable solvent containing the appropriate acid or base and isolating the salt by evaporating the solution, or by reacting the free base of compound I or II with an acid as well as reacting compound I or II having an acid group thereon with a base such that the reactions are in an organic solvent, in which case the salt separates directly or can be obtained by concentration of the solution. Salts can also be prepared by adding base to an aqueous alcohol solution of another salt.

The compounds of the invention may contain geometric isomers. Thus, the invention includes the individual isomers and mixtures thereof. The individual isomers may be prepared or isolated by methods known in the art.

The compounds of this invention may also exist in hydrated or solvated forms.

Thus, pharmaceutical compositions are prepared from the compounds of formula I and II and salts thereof described as the present invention in unit dosage form comprising the compound either alone or in admixture with a pharmaceutically acceptable carrier appropriately selected from those known.

In determining when a lipoxygenase, cyclooxygenase, or dual lipoxygenase/cyclooxygenase inhibitor is indicated of course inter alia, the particular condition in question and its severity, as well as the age, sex, weight, and the like of the subject to be treated, must be taken into consideration and this determination is within the skill of the attending physician or veterinarian.

A physician or veterinarian of ordinary skill readily determines a subject who is exhibiting symptoms of the condition, for example, allergic or inflammatory symptoms. Regardless of the route of administration selected, the compounds of the present invention are formulated into pharmaceutically acceptable dosage forms by conventional methods known to the pharmaceutical art.

The compounds can be administered in such oral unit dosage forms such as tablets, capsules, cachets, lozenges, pills, powders, or granules. They also may be administered rectally or vaginally in such forms as suppositories or bougies; they may also be introduced parenterally (e.g., subcutaneously, intravenously, or intramuscularly), using forms known to the pharmaceutical art. They are also introduced directly to an unaffected area (e.g., in the form of eye drops or by inhalation). For the treatment of allergic or inflammatory conditions such as erythema, the compounds of the present invention may also be administered topically in the form of ointments, creams, gels, or the like. In general, the preferred route of administration is orally.

An effective but nontoxic quantity of the compound of formula I or II or salt thereof is employed in treatment. The dosage regimen is selected according to a variety of factors including condition of the subject to be treated, severity of symptoms, and the route of administration. In so proceeding, the physician or veterinarian could employ relatively low dosages at first, subsequently increasing the dose until a maximum response is obtained. For convenience, the total daily dosage may be divided and administered in portions during the day if desired.

Initial dosages of the compound of the invention having formula I or II or salt thereof are ordinarily in the range of 20 mg up to 25 g per day orally, preferably 50 mg to 350 mg per dose orally, given from one to four times daily or as needed. When other forms of administration are employed, equivalent doses are administered.

A suitable dose of a compound of formula I or II or pharmaceutically acceptable salt thereof for a suffering from, or likely to suffer from any condition as described hereinbefore is 0.1 μg to 500 mg of the compound per kilogram body weight. In the case of systemic administration, the dose may be in the range of 0.5 to 500 mg of the compound per kilogram body weight, the most preferred dosage being, 0.5 to 50 mg per kilogram body weight administered two or three times daily. In the case of topical administration, e.g., to the skin or eye, a suitable dose may be in the range of 0.1 ng to 100 μg of the compound per =kilogram, typically about 0.1 μg/kg.

In the case of oral dosing for the treatment or prophylaxis of arthritis or inflammation in general, due to any cause, a suitable dose of a compound of formula I or II or a pharmaceutically acceptable salt thereof, may be as specified in the preceding paragraph, but most preferably is from 1 to 5 mg of the compound per kilogram, the most preferred dosage being from 1 to 2 mg per kilogram of body weight.

While it is possible for an active ingredient to be administered alone, it is preferable to present it as a pharmaceutical formulation comprising a compound of formula I or II or a pharmacologically acceptable acid addition or base salt thereof and a pharmacologically acceptable carrier therefor. Such formulations constitute a further feature of the present invention.

The formulations, both for veterinary and for human medical use, of the present invention comprise an active ingredient in association with a pharmaceutically acceptable carrier therefor and optionally other therapeutic ingredient(s). The carrier(s) must be "acceptable" in the sense of being compatible with the other ingredients of the formulations and not deletions to the recipient thereof.

The usefulness of the compounds of the present invention as inhibitors of the 5-lipoxygenase enzyme, cyclooxygenase, or in treating related diseases or conditions may be demonstrated by their effectiveness in various standard test procedures. A description of each procedure follows.

ARBL/ARBC WHOLE CELL 5-LIPOXYGENASE AND CYCLOOXYGENASE ASSAYS

Materials

The rat basophilic leukemia cell line (RBL-1) was obtained from the American Type Culture Collection (Rockville, Md.).

Radioimmunoassay (RIA) kits of $LTB_4$ and $PGF_{2\alpha}$ were obtained from Amersham (Arlington Heights, Ill.) and Seragen (Boston, Mass.), respectively.

All tissue culture media were obtained from GIBCO (Grand Island, N.Y.).

Method

RBL-1 cells are grown in suspension culture in Eagles minimum essential medium supplemental with 12% fetal bovine serum at 37° C. in an incubator supplied with air—5% carbon dioxide. Cells are harvested by centrifugation. They are washed with cold phosphate-buffered saline, pH 7.4 (PBS; NaCl, 7.1 g; $Na_2HPO_4$, 1.15 g; $KH_2PO_4$, 0.2 g; and KCl, 0.2 g/L). Cells are incubated with and without test agent (in DMSO) (1% DMSO is without effect on arachidonic acid metabolism) for 10 minutes at room temperature. Calcium ionophore A23187 (5 μM) is added and cells are incubated for 7 minutes at 37° C. The reaction is stopped by chilling the tubes on ice for 10 minutes. Cells are finally suspended in PBS containing 1.0 mM calcium at a density of $2 \times 10^6$ cells/mL. Cells are separated by centrifugation and the supernatant is stored at −20° C. Aliquots (100 μL) are analyzed for $LTB_4$ and $PGF_{2\alpha}$ using radioimmunoassay kits as provided by the supplier.

Table 1 contains biochemical data for compounds of formula I obtained from this whole cell assay as $IC_{50}$s which are calculated as the concentration of a test compound in micromoles (μM) causing 50% inhibition of $LTB_4$ or $PGF_{2\alpha}$ formation.

TABLE 1

| Example | ARBL[a] | ARBC[b] |
|---------|---------|---------|
| 3       | 100     | N[c]    |
| 4       | N[c]    | N[c]    |
| 10      | 2.18[d] | N[c]    |

[a] % inhibition of $LTB_4$ at 10 μM
[b] % inhibition of $PGF_{2\alpha}$ at 10 μM
[c] N = less than 40% inhibition at 10 μM
[d] $IC_{50}$ Similarly, Table 2 contains the biochemical data for compounds of formula II.

TABLE 2

| Example | ARBL[a] | ARBC[b] |
|---------|---------|---------|
| 1       | .82[d]  | 5.96[d] |
| 2       | N[c]    | N[c]    |
| 5       | N[c]    | N[c]    |
| 6       | 100     | N[c]    |
| 7       | 55      | N[c]    |
| 8       | 1.48[d] | 10.2[d] |
| 9       | N[c]    | N[c]    |
| 12      | 1.47[d] | 2.25[d] |

[a] % inhibition of $LTB_4$ at 10 μM
[b] % inhibition of $PGF_{2\alpha}$ at 10 μM
[c] N = less than 40% inhibition at 10 μM
[d] $IC_{50}$ In addition to the compound of formula I or II or salt thereof, the pharmaceutical compositions can also contain other active ingredients, such as cyclooxygenase inhibitors, nonsteroidal antiinflammatory drugs (NSAIDs), peripheral analgesic agents such as zomepirac, diflunisal, and the like. The weight ratio of the compound of the formula I or II or salt thereof to the second active ingredient may be varied and will depend upon the effective dose of each ingredient. Generally, an effective dose of each will be used. Thus, for example, when a compound of the formula I or II is combined with an NSAID, the weight ratio of the formula I or II to the NSAID will generally range from about 1000:1 to about 1:1000, preferably about 200:1 to 1:200. Combinations of a compound of the formula I or II or salt thereof and other active ingredients will generally also be within the aforementioned range, but in each case, an effective dose of each active ingredient should be used.

Combinations of a compound of the formula I or II or salt thereof and other active ingredients will generally be in the aforementioned ratios.

NSAIDs can be characterized into five groups:

(1) the propionic acid derivatives;
(2) the acetic acid derivatives;
(3) the fenamic acid derivatives;
(4) the biphenylcarboxylic acid derivatives; and
(5) the oxicams or a pharmaceutically acceptable salt thereof.

The propionic acid derivatives which may be used comprise: ibuprofen, ibuprofen aluminum, indoprofen, ketoprofen, naproxen, benoxaprofen, flubiprofen, fenoprofen, fenbufen, pirprofen, earprofen, oxaprozin, pranoprofen, miroprofen, tioxaprofen, suprofen, alminoprofen, tiaprofen, fluprofen, and bucloxic acid. Structurally related propionic acid derivatives having similar analgesic and antiinflammatory properties are also intended to be included in this group.

Thus, "propionic acid derivatives" as defined herein are nonnarcotic analgesics/nonsteroidal antiinflammatory drugs having a free —CH(CH₃)COOH or —CH₂CH₂COOH group (which optionally can be in the form of a pharmaceutically acceptable salt group, e.g., —CH(CH₃)COO⁻Na⁺or —CH₂CH₂COO⁻Na⁺), typically attached directly or via a carbonyl function to a ring system, preferably to an aromatic ring system.

The acetic acid derivatives which may be used comprise: indomethacin, which is a preferred NSAID, sulindac, tolmetin, zomepirac, diclofenac, fenelofenac, alclofenac, ibufenac, isoxepac, furofenac, tiopinac, zidometacin, acemetacin, fentiazac, clidanac, oxpinae, and fenclozic acid. Structurally related acetic acid derivatives having similar analgesic and antiinflammatory properties are also intended to be encompassed by this group.

Thus "acetic acid derivatives" as defined herein are nonnarcotic analgesics/nonsteroidal antiinflammatory drugs having a free —CH₂COOH group (which optionally can be in the form of a pharmaceutically acceptable salt group e.g. —CH₂COO⁻Na⁺) typically attached directly to a ring system preferably to an aromatic or hetero aromatic ring system.

Thus "fenamic acid derivatives" as defined herein are nonnarcotic analgesics/nonsteroidal antiinflammatory drugs which contain the basic structure:

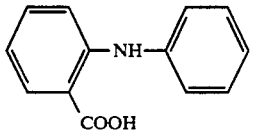

which can bear a variety of substituents and in which the free —COOH group can be in the form of a pharmaceutically acceptable salt group e.g. —COO⁻Na⁺·

The biphenylcarboxylic acid derivatives which can be used comprise: diflunisal and flufenisal. Structurally related biphenylcarboxylic acid derivatives having similar analgesic and antiinflammatory properties are also intended to be encompassed by this group.

Thus "biphenylcarboxylic acid derivatives" as defined herein are nonnarcotic analgesics/nonsteroidal antiinflammatory drugs which contain the basic structure:

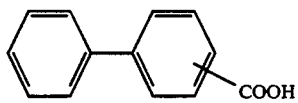

which can bear a variety of substituents and in which the free —COOH group can be in the form of a pharmaceutically acceptable salt group e.g. —COO⁻Na⁺·

The oxicams which can be used in the present invention comprise: piroxicam, sudoxicam, isoxicam, and 4-hydroxyl-1,2-benzothiazine-1,1-dioxide 4-(N-phenyl)-carboxamide. Structurally related oxicams having similar analgesic and antiinflammatory properties are also intended to be encompassed by this group.

Thus "oxicams" as defined herein are nonnarcotic analgesics/nonsteroidal antiinflammatory drugs which have the general formula:

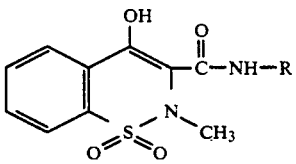

wherein R is an aryl or heteroaryl ring system.

The following NSAIDs may also be used: acemetacin, alminoprofen, amfenac sodium, aminoprofen, anitrazafen, antrafenine, auranofin, bendazac lysinate, benzydamine, beprozin, broperamole, bufezolac, carprofen, cinmetacin, ciproquazone, clidanac, cloximate, dazidamine, deboxamet, delmetacin, detomidine, dexindoprofen, diacerein, di-fisalamine, difenpyramide, emorfazone, enfenamic acid, enolicam, epirizole, etersalate, etodolac, etofenamate, fanetizole mesylate, fenclofenac, fenclorac, fendosal, fenflumizole, fentiazac, feprazone, floctafenine, flunixin, flunoxaprofen, fluproquazone, fopirtoline, fosfosal, furcloprofen, furofenac, glucametacin, guaimesal, ibuproxam, isofezolac, isonixim, isoprofen, isoxepac, isoxicam, lefetamine HCl, leflunomide, lofemizole, lonazolac calcium, lotifazole, loxoprofen, lysin, clonixinate, meclofenamate sodium, meseclazone, microprofen, nabumetone, nictindole, nimesulide, orpanoxin, oxametacin, oxapadol, oxaprozin, perisoxal citrate, pimeprofen, pimetacin, piproxen, pirazolac, pirfenidone, pirprofen, pranoprofen, proglumetacin maleate, proquazone, pyridoxiprofen, sudoxicam, suprofen, talmetacin, talniflumate, tenoxicam, thiazolinobutazone, thielavin B, tiaprofenic acid, tiaramide HCl, tiflamizole, timegadine, tioxaprofen, tolfenamic acid, tolpadol, tryptamid, ufenamate, and zidometacin.

Finally NSAIDs which may also be used include the salicylates, specifically aspirin and the phenylbutazones and pharmaceutically acceptable salts thereof.

Pharmaceutical compositions comprising the formula I or II compounds or salt thereof may also contain as the second active ingredient antihistaminic agents such as benadryl, dramamine, histadyl, phenergan, and the like. Alternatively, they may include prostaglandin antagonists such as those disclosed in European patent application 11,067 or thromboxane antagonists such as those disclosed in U.S. Pat. No. 4,237,160. They may also contain histidine decarboxylase inhibitors such as α-fluoromethylhistidine, described in U.S. Pat. No. 4,325,961. The compounds of formula I or II or salt thereof may also be advantageously combined with an H₁ or H₂-receptor antagonist such as for instance cimetidine, ranitidine, terfenadine, famotidine, temelastine, acrivastine, loratidine, cetrizine, tazifylline, azelastine, aminothiadiazoles disclosed in European Pat. 81102976.8 and like compounds such as those disclosed in U.S. Pat. Nos. 4,283,408; 4,362,736; 4,394,508; and European patent application 40,696. The pharmaceutical compositions may also contain a K⁺/H⁺—ATPase inhibitor such as omeprazole, disclosed in U.S. Pat. No. 4,255,431 and the like. Each of the references referred to in this paragraph is hereby incorporated by reference.

Generally, a scheme for preparation of the compounds of the formula I above is as follows:

SCHEME 1

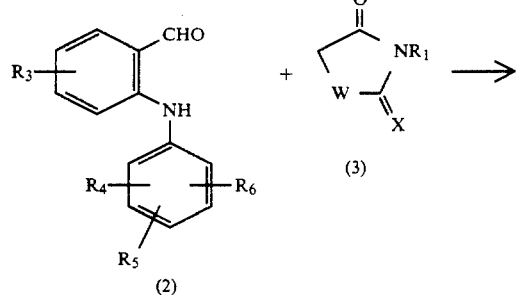
(2) + (3)

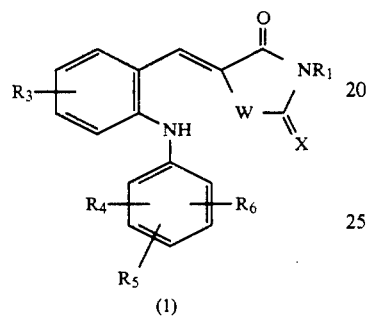
(1)

wherein W, X, $R_1$, $R_3$, $R_4$, $R_5$, and $R_6$ are as defined above.

A general method of preparation of these compounds is condensation of the aldehyde (2) with an active methylene containing compound (3). This condensation can be performed in an alcoholic solvent such as ethanol or methanol, or the like in the presence of either a base such as ammonia, piperidine, or the like or with a catalytic amount of a mineral acid such as $H_2SO_4$, HCl, or the like.

Alternatively acetic acid is used as the solvent with either anhydrous sodium acetate or preferably β-alanine. The reactants are heated at reflux for several hours.

This procedure can also be used to prepare compounds of the formula II where Y is SH, OH or NHz by reacting the aldehyde (2) above with

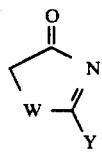
(4)

which is a compound containing an active methylene group.

A procedure for the preparation of the compound of formula II when Y is OH, $SR_1$, $S(O)_n$ $R_1$, $NR_1R_2$, $NHCN_1$, $NHC(X)NHR_2$, $NR_2(OR_2)$, $NHNHC(S)NH_2$ or $NHNHC(NH)NH_2$ is as follows:

SCHEME 2

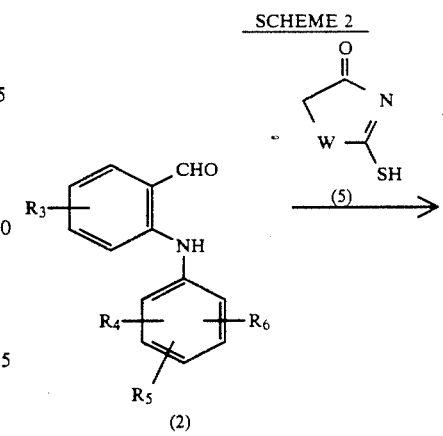
(2) + (5)

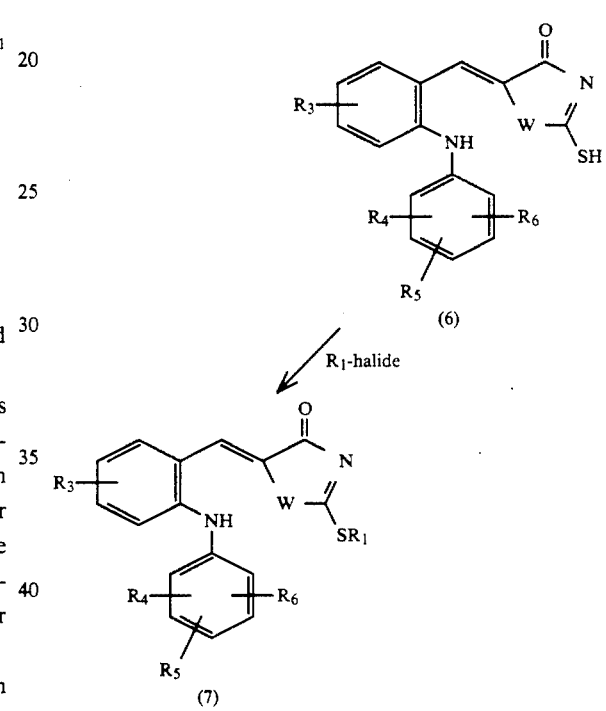
(6) → (7)

wherein W, $R_1$, $R_3$, $R_4$, $R_5$ and $R_6$ are as defined above. An alkyl halide is reacted with compounds of formula (6) in the presence of an organic base, preferably diisopropylethylamine in an etheral solvent such as dioxane or preferably in an alcoholic solvent such as methanol to give compounds of formula (7). Compound (7) is then treated with an amine in a solvent such as DMF or in an alcoholic solvent, preferably t-butanol at elevated temperature in the presence or absence of potassium t-butoxide to give compounds of formula II wherein Y is $NR_1R_2$, NHCN, NHC(x)$NHR_2$, $NR_2(OR_2)$, $NHNHC(S)NH_2$, $NHNHC(NH)NH_2$. Alternatively, compound (7) is treated with an oxidizing agent, preferably m-CPBA to provide compounds of formula II wherein Y is $S(O)R_2$ if one equivalent of oxidizing agent is used or wherein Y is $S(0)_2R_2$ if two equivalents of oxidizing agent are used. Alternatively, compound (7) is treated with an aqueous mineral acid, preferably HCl in an etheral solvent, preferably THF to give compounds of formula II wherein Y is OH.

Compounds of type I and II that contain an acidic proton can be treated with organic and inorganic bases such as NaOH, choline, or the like to form salts.

Conditions within the description of Schemes 1 and 2 above and variations in the description are known or can be readily determined from analogous reactions known to one of ordinary skill in the art.

Generally, starting materials are known, commercially available, or can be prepared by known methods. In particular, see U.S. Pat. No. 4,981,865. The preparation of 2-[[(3,5-Bis(1,1-dimethylethyl)-4hydroxyphenyl)]amino]benzoic acid methyl ester is outlined in Example 13.

Under certain circumstances as discussed above, it is necessary to protect either the N or O of intermediates. Introduction and removal of such suitable oxygen and nitrogen protecting groups are well-known in the art of organic chemistry; see for example, "Protective Groups in Organic Chemistry," J. F. W. McOmie, *Advances in Organic Chemistry*, Vol. 3, 159–190 (1963); J. F. W. McOmie, *Chem. and Ind.*, 603 (1979), and T. W. Greene, "Protective Groups in Organic Synthesis," Wiley (New York) 1981, Chapters 2, 3, and 7.

Examples of suitable oxygen protecting groups are benzyl, t-butyldimethysilyl, ethoxyethyl, methoxyethoxymethyl, and the like. Protection of an N—H containing moiety is necessary for some of the processes described herein for the preparation of compounds of this invention. Suitable nitrogen protecting groups are benzyl, triphenylmethyl, trialkylsilyl, trichloroethylcarbamate, trichloroethoxycarbonyl, vinyloxycarbamate acetyl, and the like.

Under certain circumstances, it is necessary to protect two different oxygens with dissimilar protecting groups such that one can be selectively removed while leaving the other in place. The benzyl and t-butyldimethylsilyl groups are used in this way; either is removable in the presence of the other, benzyl being removed by catalytic hydrogenolysis, and t-butyldimethylsilyl be removed by reaction with, for example, tetra-n-butylammonium fluoride.

In the process described herein for the preparation of compounds of this invention, the requirements for protective groups are generally well recognized by one skilled in the art of organic chemistry, and accordingly the use of appropriate protecting groups in necessarily implied by the processes of the schemes herein, although not expressly illustrated.

The products of the reactions described herein are isolated by conventional means such as extraction, distillation, chromatography, and the like.

The invention is further elaborated by the representative examples as follows. Such examples are not meant to be limiting.

EXAMPLE 1

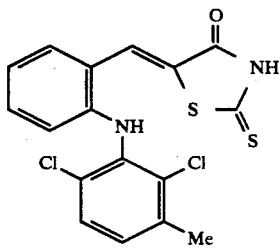

(Z)-5-[[2-[(2,6-Dichloro-3-methylphenyl)amino]-phenyl]methylene]-2-thioxo-4-thiazolidinone To a room temperature solution of 2-[(2,6-dichloro-3-methylphenyl)amino]benzaldehyde (209 mg, 0.75 mmols) and rhodanine (104 mg, 0.78 mmols) in 15 mL of acetic acid is added β-alanine (48 mg, 0.54 mmols). The solution is heated at reflux for one hour. During this time a thick precipitate forms. The mixture is filtered hot, washing with an additional 5 mL of [[2- [(2,6-dichloro-3-methylphenyl)amino]phenyl]methylene]-2-thioxo-4-thiazolidinone as a fluffy orange solid; mp 274°-276° C. dec.

Calc'd for $C_{17}H_{12}Cl_2N_2OS_2$:
C, 51.64; H, 3.06; Cl, 17.94; N, 7.09;
S, 16.22. Found: C, 51.30; H, 2.93; Cl, 18.13; N, 6.85; S, 16.08

EXAMPLE 2

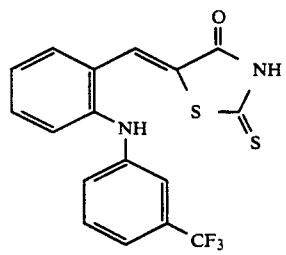

(Z)-2-Thioxo-5-[[2-[[3-(trifluoromethyl)phenyl]amino]-phenyl]methylene]-4-thiazolidinone To a room temperature solution of 2-[[3-(trifluoromethyl)phenyl]amino]benzaldehyde (749 mg, 2.83 mmols) and rhodanine (398 mg, 2.99 mmols) in 20 mL of acetic acid is added β-alanine (382 mg, 4.29 mmols). The solution is heated at reflux for 45 min. During this time a thick precipitate forms. The mixture is filtered hot, washing with an additional 10 mL of acetic acid, to provide 715 mg (66%) of (Z)-2-thioxo-5-[[2-[[3-(trifluoromethyl)phenyl]amino]phenyl]methylene]-4-thiazolidinone as a bright red-orange solid; mp=234°-236° C. Calc'd for $C_{17}H_{11}F_3N_2OS_2$:

C, 53.67; H, 2.62; N, 7.37. Found: C, 53.41; H, 2.85; N, 7.36.

EXAMPLE 3

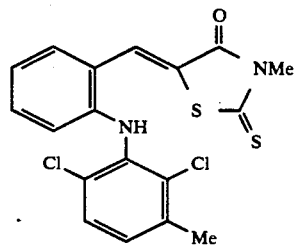

(Z)-5-[[2-[(2,6-Dichloro-3-methylphenyl)amino]-phenyl]methylene]-3-methyl-2-thioxo-4-thiazolidinone To a room temperature solution of 2-[(2,6-dichloro-3-methylphenyl)amino]benzaldehyde (276 mg, 0.99 mmols) and 3-methylrhodanine (166 mg, 1.13 mmols) in 15 mL of acetic acid is added β-alanine (102 mg, 1.14 mmols). The solution is heated at reflux for 3.5 h. The solution is cooled to room temperature and the resulting precipitate is collected by filtration to provide 258 mg (64%) of (Z)-5-[[2-[(2,6-dichloro-3-methylphenyl-)amino]phenyl]methylene]-2-thioxo-4-thiazolidinone as a bright orange solid; mp=175°-176° C. Calc'd for C₁₈H₁₄Cl₂N₂OS₂:

C, 52.81; H, 3.45; N, 6.85. Found: C, 52.45; H, 3.22; N, 6.58.

EXAMPLE 4

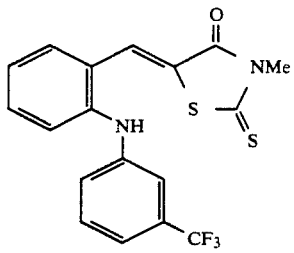

(Z)-3-Methyl-2-thioxo-5-[[2-[[3-(trifluoromethyl)-phenyl]amino]phenylmethylene]-4-thiazolidinone To a room temperature solution of 2-[[3-(trifluoromethyl)phenyl]amino]benzaldehyde (623 mg, 2.35 mmols) and 3-methylrhodanine (379 mg, 2.58 mmols) in 20 mL of acetic acid is added β-alanine (314 mg, 3.53 mmols). The solution is heated at reflux for 3 hours. The mixture is cooled to room temperature and the precipitate is collected by filtration to provide 226 mg (24%) of a bright orange solid. The filtrate is reduced slightly in volume to provide an additional 213 mg (23%) of product. Recrystallization from hexane provides analytically pure (Z)-3-methyl-2-thioxo-5-[[2-[[3-(trifluoromethyl)-phenyl]amino]phenylmethylene]-4-thiazolidinone; mp=142°-144° C.

Calc'd for C₁₈H₁₃F₃N₂OS₂:

C, 54.81; H, 3.32; N, 7.10. Found: C, 54.56; H, 3.02; N, 6.90.

EXAMPLE 5

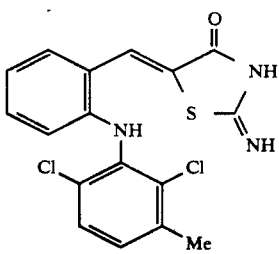

(Z)-5-[[2-[(2,6-Dichloro-3-methylphenyl)amino]-phenyl]methylene]-2-imino-4-thiazolidinone To a room temperature suspension of 2-[(2,6-dichloro-3-methylphenyl)amino]benzaldehyde (468 mg, 1.67 mmols) and pseudothiohydantoin (800 mg, 6.90 mmols) in 15 mL of acetic acid is added β-alanine (153 mg, 1.71 mmols). The mixture is heated at reflux for 4.5 h, during which time solution occurs. The solution is cooled to room temperature and the resulting precipitate is collected by filtration to provide 460 mg (73%) of a bright yellow-orange solid. An analytical sample of (Z)-5-[[2-[(2,6-dichloro-3methylphenyl)amino]phenyl]-methylene]-2-imino-4-thiazolidinone is obtained by recrystallization from acetonitrile; mp 235°-238° C.

Calc'd for C₁₇H₁₃Cl₂N₃OS-.25H₂O:

C, 53.34; H, 3.55; N, 10.98. Found: C, 53.40; H, 3.22; N, 11.01

EXAMPLE 6

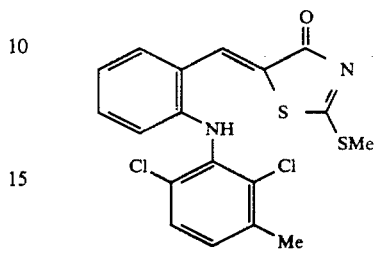

(Z)-5-[[2-[(2,6-Dichloro-3-methylphenyl)amino]-phenyl]methylene]-2-(methylthio)-4(5H)-thiazolone To room temperature suspension of (Z)-5-[[2-[(2,6-dichloro-3-methylphenyl)amino]phenyl]methylene]-2-thioxo-4-thiazolidinone (3.177 g, 8.04 mmols) in 125 mL of ethanol is added Hunig's base (1.57 mL, 9.03 mmols) followed by iodomethane (600 μL, 9.63 mmols). After stirring at room temperature overnight the yellow solid is collected by filtration to give 2.861 g (87%) of (Z)-5-[[2-[(2,6-dichloro-3-methylphenyl)amino]phenyl]methylene]-2-(methylthio)-4(5 H)-thiazolone. An analytical sample is obtained by recrystallization from hexane-ethyl acetate; mp 233°-236° C. Calc'd for C₁₈H₁₄Cl₂N₂OS₂:

C, 52.81; H, 3.45; N, 6.85. Found: C, 52.69; H, 3.28; N, 6.63.

EXAMPLE 7

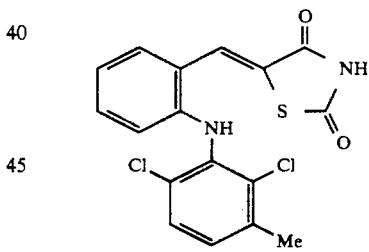

(Z)-5-[[2-[(2,6-Dichloro-3-methylphenyl)amino]-phenyl]methylene]-2,4-thiazolidinedione To room temperature solution of (Z)-5-[[2-[(2,6-dichloro -3 methylphenyl)amino]phenyl]methylene]-2-(methylthio)-4(5 H)-thiazolone (415 mg, 1.02 mmols) in 20 mL of tetrahydrofuran is added 20 mL of 10% aqueous hydrochloric acid. The mixture is heated at reflux for 2 h, then allowed to cool to room temperature. The solid is collected by filtration, washing with water. Drying in vacuo overnight at 65° C. provides 214 mg (56%) of (Z)-5-[[2-[(2,6-dichloro-3-methylphenyl-)amino]phenyl]methylene]-2,4-thiazolidinedione as a yellow solid; mp=269°-270° C. dec. Calc'd for C₁₇H₁₂Cl₂N₂O₂S:

C, 53.84; H, 3.19; Cl, 18.70; N, 7.39; S, 8.45. Found: C, 53.52; H, 2.95; Cl, 18.79; N, 7.24; S, 8.54.

The aqueous filtrate is extracted with ethyl acetate, washed with saturated sodium bicarbonate, followed by brine. Concentration and recrystallization of the residue provides an additional 103 mg (27%) of product as a fluffy yellow solid.

Found: C, 53.86; H, 3.29; N, 7.41.

EXAMPLE 8

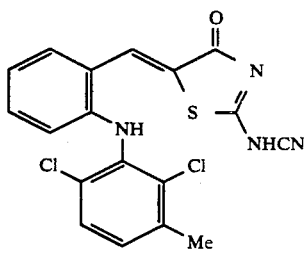

(Z)-5-[[2-[(2,6-Dichloro-3-methylphenyl)amino]phenyl]methylene]-4,5-dihydro-4-oxo-2-thiazolyl]-cyanamide A room temperature suspension of potassium t butoxide (85 mg, 0.76 mmols) and cyanamide (120 mg, 2.85 mmols) in 5 mL of t-butanol is stirred for 10 minutes. (Z)-5-[[2-[(2,6-Dichloro-3-methylphenyl)amino]phenyl]methylene]-2-(methylthio)-4(5 H)thiazolone (270 mg, 0.66 mmols) is added and the mixture is heated to reflux and then cooled. The mixture is partitioned between water and 1:1 hexane: ethyl acetate. The aqueous layer is acidified with 10% aqueous hydrochloric acid and the resultant yellow solid is collected by filtration, washing with water to give 174 mg (65%). Recrystallization from acetonitrile provides an analytical sample of (Z)-5-[[2-[(2,6-dichloro-3-methylphenyl)-amino]phenyl]methylene]-4,5-dihydro-4-oxo-2-thiazolyl]-cyanamide; mp 250°-251° C.

Calc'd for $C_{18}H_{12}Cl_2N_4OS$:

C, 53.61; H, 3.00; N, 13.89. Found: C, 53.21; H, 2.83; N, 13.64.

EXAMPLE 9

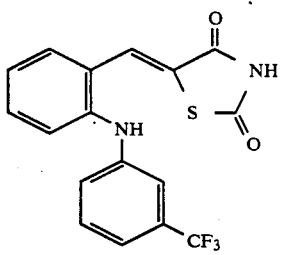

(Z)-5-[[2-[[3-(Trifluoromethyl)phenyl]amino]phenyl]methylene]-2,4-thiazolidinedione To a room temperature solution of (Z)-2-methylthio-5-[[2-[[3-(trifluoromethyl)phenyl]amino]phenyl]methylene]-4(5 H)-thiazolone (507 mg, 1.28 mmols) in 14 mL of tetrahydrofuran is added 14 mL of 10% aqueous hydrochloric acid. The mixture is heated at reflux for 30 minutes, then allowed to cool to room temperature. The mixture is partitioned between water and ethyl acetate. The organic phase is washed with saturated aqueous sodium bicarbonate followed by brine, then dried over magnesium sulfate, filtered, and concentrated in vacuo to provide 390 mg (83%) of (Z)-5-[[2-[[3-(trifluoromethyl)phenyl]amino]phenyl]methylene]-2,4-thiazolidinedione. An analytical sample is obtained by recrystallization from ethyl acetate and hexane; mp 213°-214° C. dec.

Calc'd for $C_{17}H_{11}F_3N_2O_2S$:

C, 56.04; H, 3.04; N, 7.69; S, 8.80. Found: C, 55.91; H, 2.95; N, 7.57; S, 8.78.

EXAMPLE 10

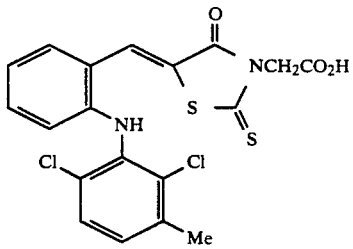

(Z)-5-[[2-[[2-Dichloro-3-methylphenyl)-amino]phenyl]methylene]-4-oxo-2-thioxo-3-thiazolidine acetic acid To a room temperature solution of 2-[(2,6-dichloro-3-methylphenyl)amino]benzaldehyde (400 mg, 1.56 mmols) in 15 mL of acetic acid is added β-alanine (121 mg, 1.36 mmols). The solution is heated at reflux for three hours then cooled to room temperature. The resulting orange solid is filtered, washing with an additional 10 mL of acetic acid, then hexane, to provide 501 mg (78%) of (Z)-5-[[2-[(2,6-dichloro-3-methylphenyl)-amino]phenyl]methylene -4-oxo-2-thioxo-3-thiazolidine acetic acid. An analytical sample is obtained by suspending a sample in boiling ethyl acetate and filtering while hot; mp=270°-272° C. dec.

Calc'd for $C_{19}H_{14}Cl_2N_2O_3S_2$:

C, 50.33; H, 3.11; Cl, 15.64; N, 6.18; S, 14.14. Found: C, 50.40; H, 2.89; Cl, 15.64; N, 6.06; S, 14.40

EXAMPLE 11

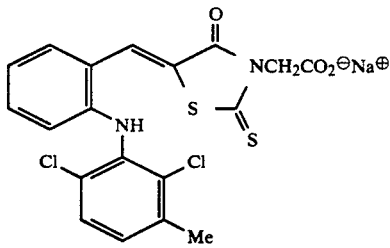

Sodium salt of (Z)-5-[[2-[(2,6-dichloro-3-methylphenyl)-amino]-phenyl]methylene]-4-oxo-2-thioxo-3-thiazolidine acetic acid To a room temperature suspension of (Z)-5-[[2-[(2,6-dichloro-3-methylphenyl)amino]phenyl]methylene]-4-oxo-2-thioxo-3-thiazolidine acetic acid (352 mg, 0.78 mmols) in 15 mL of methanol is added 0.76 mL of 1 N aqueous sodium hydroxide. The suspension is stirred at room temperature for 3.5 h. The solids are removed by filtration and the filtrate is concentrated and dried in vacuo to provide 197 mg (54%) of the sodium salt of (Z)-5-[[2-[(2,6-dichloro-3-methylphenyl)-amino]-phenyl]methylene-4-oxo-2-thioxo-3-thiazolidine acetic acid; mp=248°-250° C.

Calc'd for $C_{19}H_{13}Cl_2N_2O_3S_2Na \cdot 2H_2O$:
C, 44.62; H, 3.35; N, 5.48. Found: C, 44.31; H, 3.00; N, 5.12.

EXAMPLE 12

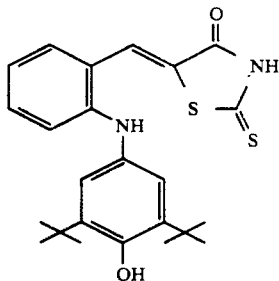

5-[(2-[3,5-Bis[1,1-dimethylethyl]-4hydroxyphenyl-)amino]phenyl)methylene]-2-thioxo-4-thiazolidinone 2-[3,5-Bis[1,1-dimethylethyl]-4-hydroxyphenyl-)amino]benzaldehyde (1.3 g, 4.0 mmols), rhodanine (5.3 g, 4.0 mmols) and β-alanine (0.7 g, 8.0 mmols) are dissolved in 20 mL of acetic acid and warmed in a 120° C. oil bath for 1.5 hours. The reaction is cooled to room temperature and diluted with 400 mL of diethyl ether. The organic layer is washed with five 200 mL portions of brine, then dried over magnesium sulfate and evaporated. The residue is purified by flash chromatography in 25% (v/v) diethyl ether/chloroform. Subsequent recrystallization from isopropyl ether/hexane gives 0.36 g (20%) of 5-[(2-[3,5-bis[1,1-dimethylethyl]-4-hydroxyphenyl)amino]phenyl)methylene]-2-thioxo-4-thiazolidinone, mp 218°-219° C.

Calc'd for $C_{24}H_{28}N_2O_2S_2$:
C, 65.41; H, 6.42; N, 6.36; S, 14.55. Found: C, 65.46; H, 6.43; N, 6.25; S, 14.60.

EXAMPLE 12A

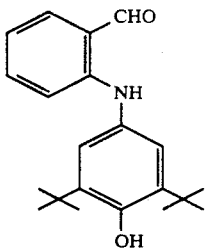

2-[(3,5-Bis[1,1-dimethylethyl]-4-hydroxyphenyl)amino]benzaldehyde

2-[(3,5-Bis[1,1-dimethylethyl]-4-hydroxyphenyl-)amino]-benzoic acid methyl ester (1.1 g, 3.1 mmols) is dissolved in 100 mL of diethyl, ether and added to a suspension of lithium aluminum hydride (0.46 g, 12.4 mmols) in 20 mL of diethyl ether at room temperature under an argon atmosphere. After 30 minutes the reaction is quenched with 0.46 mL of water, followed by 0.46 mL of 15% (w/v) aqueous sodium hydroxide and then 1.38 mL of water. The solids are removed by filtration of the reaction mixture into a flask containing sodium dithionite (15 g) and 300 mL of 50% aqueous tetrahydrofuran. The filtrate is concentrated in vacuo and the organics are extracted into two 100 mL portions of methylene chloride. The methylene chloride extracts are washed with 100 mL of brine, dried over magnesium sulfate, and filtered. The filtrate is added to a suspension of pyridinium chlorochromate (2.0 g, 9.3 mmols) and alumina (7.0 g) in 100 mL of methylene chloride. The reaction is stirred at room temperature for 12 hours, then filtered through a silica gel pad which is washed with 100 mL of diethyl ether. The filtrate is concentrated in vacuo and the residue is taken up in 100 mL of tetrahydrofuran. Sodium dithionite (15 g) is dissolved in 100 mL of water and added to the tetrahydrofuran solution. After 15 minutes the mixture is concentrated in vacuo and then extracted with three 50 mL portions of diethyl ether. The ether extract is washed with 50 mL of brine and dried over magnesium sulfate. Evaporation gives 1.0 g (100%) of 2-[(3,5-bis[1,1-dimethylethyl]-4-hydroxyphenyl)amino]benzaldehyde, mp 105°-107° C. An analytical sample is obtained by recrystallization from water/methanol.

Calc'd for $C_{21}H_{27}NO_2$:
C, 77.49; H, 8.38; N, 4.30. Found: C, 77.27; H, 8.46; N, 4.04.

EXAMPLE 13

2-[[(3,5-bis(1,1-dimethylethyl)-4-hydroxyphenyl)-]amino]benzoic acid methyl ester Titanium tetrachloride (28.8 mL, 1.0 M in $CH_2Cl_2$) is added dropwise to a stirred solution of pyridine (12.0 mL) in $CH_2Cl_2$ (100 mL) at 0° C. The resulting suspension is added to a solution of methyl anthranilate (6.8 g, 45.4 mmol) and 2,6-bis(1,1-dimethylethyl)-p-benzoquinone (10.0 g, 45.4 mol) in dry THF (200 mL). The reaction mixture is warmed to reflux under an argon atmosphere for four hours. At this time, another $TiCl_4$/pyridine suspension (prepared as above) is added. The reaction mixture is warmed at reflux for an additional 12 hours. It is cooled and filtered through Celite to remove the suspended solid. The solid is washed with ethyl acetate (100 mL) and the combined filtrates are evaporated. The residue is taken up in 200 mL of THF and stirred vigorously with a solution of sodium dithionite (100 g) in water (100 mL) for 30 minutes. The layers are separated and the aqueous layer is extracted with ethyl acetate (3×100 mL). The organic layers are combined, washed with brine (2×100 mL), dried over magnesium sulfate, and evaporated to give 2-[[(3,5-bis(1,1-dimethylethyl)-4-hydroxyphenyl)]amino]benzoic acid methyl ester; mp 155°-158° C.

We claim:
1. A compound of the formula (I)

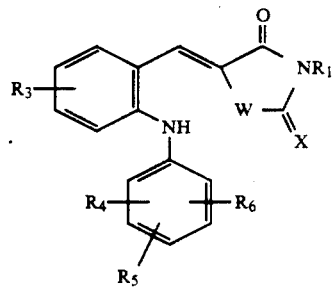

and a pharmaceutically acceptable salt thereof; wherein
(1) X is oxygen, sulfur, or NH;
(2) W is sulfur;

(3) R$_1$ is lower alkyl or CH$_2$COOR$_2$ wherein R$_2$ is as defined above;
(4) R$_3$, R$_4$, R$_5$, and R$_6$ are independently
  i) hydrogen;
  ii) fluorine;
  iii) chlorine;
  iv) bromine;
  v) iodine;
  vi) trifluoromethyl
  vii) lower alkyl;
  viii) CN;
  ix) hydroxy;
  x) lower alkoxy;
  xi) NO$_2$;
  xii) NR$_7$R$_8$ wherein R$_7$ and R$_8$ are independently hydrogen, lower alkyl or acyl;
  xiii) S(O)$_n$- lower alkyl wherein n is an integer of 0–2.

2. A compound of claim 1 wherein W is sulfur and X, R$_1$, R$_2$, R$_3$, R$_4$, R$_5$, R$_6$, R$_7$, R$_8$, and n are as defined above.

3. A compound of claim 2 which is (Z)-5-[[2-[(2,6-dichloro-3-methyl(phenyl)amino]phenyl]methylene]-3-methyl-2-thioxo-4-thiazolidinone.

4. A compound of claim 2 which is (Z)-3-methyl-2-thioxo-5-[[2-[[3-(trifluoromethyl)phenyl]amino]phenyl-methylene]-4-thiazolidinone.

5. A compound of claim 2 which is (Z)-5-[[2-[(2,6-dichloro-3-methylphenyl)amino]phenyl]methylene]4-oxo-2-thioxo-3-thiazolidine acetic acid.

6. A compound of claim 2 which is the sodium salt of (Z)-5-[[2-[(2,6-dichloro-3-methylphenyl)amino]phenyl]-methylene]-4-oxo-2-thioxo-3-thiazolidine acetic acid.

7. A compound of the formula (II)

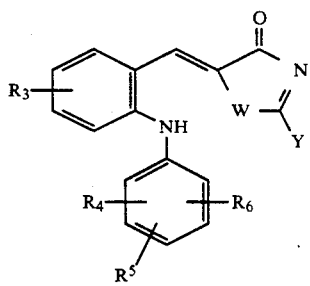

II and a pharmaceutically acceptable salt thereof; wherein
(1) Y is
  i) OH;
  ii) SH;
  iii) NH$_2$;
  iv) SR$_9$ wherein R$_9$ is lower alkyl or CH$_2$COOR$_{10}$ wherein R$_{10}$ is hydrogen or lower alkyl;
  v) S(O)$_n$R$_9$ wherein n is 0, 1, or 2; and R$_9$ are as defined above;
  vi) NR$_9$R$_{10}$ wherein R$_9$ and R$_{10}$ are as defined above;
  vii) NHCN;
  viii) NHC(X)NHR$_{10}$ wherein X and R$_{10}$ are as defined above;
  ix) NR$_{10}$(OR$_{11}$) wherein R$_{10}$ is as defined above and R$_{11}$ is hydrogen or lower alkyl;
  x) NHNHC(S)NH$_2$;
  xi) NHNHC(NH)NH$_2$;
(2) W is sulfur;
(3) R$_3$, R$_4$, R$_5$ and R$_6$ are independently
  i) hydrogen;
  ii) fluorine;
  iii) chlorine;
  iv) bromine;
  v) iodine;
  vi) trifluoromethyl
  vii) lower alkyl;
  viii) CN;
  ix) hydroxy;
  x) lower alkoxy;
  xi) NO$_2$;
  xii) NR$_7$R$_8$ wherein R$_7$ and R$_8$ are independently hydrogen, lower alkyl or acyl;
  xiii) S(O)$_n$ - lower alkyl wherein n is an integer of 0–2.

8. A compound of claim 7 wherein W is sulfur and Y, R$_1$, R$_2$, R$_3$, R$_4$, R$_5$, R$_6$, R$_9$, R$_{10}$, and n are as defined above.

9. A compound of claim 8 which is (Z)-5-[[2-[(2,6-dichloro-3-methylphenyl)amino]phenyl]methylene]-2-thioxo-4-thiazolidinone.

10. A compound of claim 8 which is (Z)-2-thioxo-5-[[2-[[3-trifluoromethyl)phenyl]amino]phenyl]methylene]-4-thiazolidinone.

11. A compound of claim 8 which is (Z)-5-[[2-[(2,6-dichloro-3-methylphenyl)amino]phenyl]methylene]-2-imino-4-thiazolidinone.

12. A compound of claim 8 which is (Z)-5-[[2-[(2,6-dichloro-3-methylphenyl)amino]phenyl]methylene]-2-(methylthio)-4(5 H)-thiazolone.

13. A compound of claim 8 which is (Z)-5-[[2-[(2,6-dichloro-3-methylphenyl)amino]phenyl]methylene]-2,4-thiazolidinedione.

14. A compound of claim 8 which is (Z)-5-[[2-[(2,6-dichloro-3-methylphenyl)amino]phenyl]methylene]-4,5-dihydro-4-oxo-2thiazolyl]-cyanamide.

15. A compound of claim 8 which is (Z)-5-[[2-[[3-(trifluoromethyl)phenyl]amino]phenyl]methylene]-2,4-thiazolidinedione.

16. A compound of claim 8 which is 5-[(2-[3,5-bis[1,1-dimethylethyl]-4-hydroxyphenyl)amino]phenyl)methylene]-2-thioxo-4-thiazolidinone.

17. A pharmaceutical composition for treating inflammation comprising an antiinflammatory amount of a compound of claim 1 with a pharmaceutically acceptable carrier.

18. A pharmaceutical composition for treating inflammation comprising an antiinflammatory amount of a compound of claim 7 with a pharmaceutically acceptable carrier.

19. A method of treating inflammation in a subject suffering therefrom comprising administration of a compound of claim 1 in unit dosage form.

20. A method of treating inflammation in a subject suffering therefrom comprising administration of a compound of claim 7 in unit dosage form.

* * * * *